(12) United States Patent
Gerk et al.

(10) Patent No.: US 9,616,033 B2
(45) Date of Patent: Apr. 11, 2017

(54) SELECTIVE METABOLIC APPROACH TO INCREASING ORAL BIOAVAILABILITY OF PHENYLEPHRINE AND OTHER PHENOLIC BIOACTIVITIES

(71) Applicant: VIRGINIA COMMONWEALTH UNIVERSITY, Richmond, VA (US)

(72) Inventors: Phillip M. Gerk, Richmond, VA (US); William H. Barr, Richmond, VA (US); Joseph K. Ritter, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/345,689

(22) PCT Filed: Sep. 27, 2012

(86) PCT No.: PCT/US2012/057588
§ 371 (c)(1),
(2) Date: Mar. 19, 2014

(87) PCT Pub. No.: WO2013/049365
PCT Pub. Date: Apr. 4, 2013

(65) Prior Publication Data
US 2014/0221426 A1 Aug. 7, 2014

Related U.S. Application Data

(60) Provisional application No. 61/539,530, filed on Sep. 27, 2011, provisional application No. 61/544,396, filed on Oct. 7, 2011.

(51) Int. Cl.
| | |
|---|---|
| A61K 31/137 | (2006.01) |
| A61K 31/375 | (2006.01) |
| A61K 31/235 | (2006.01) |
| A61K 31/121 | (2006.01) |
| A61K 31/353 | (2006.01) |
| A61K 45/06 | (2006.01) |
| A61K 31/05 | (2006.01) |
| A61K 31/085 | (2006.01) |
| A61K 31/09 | (2006.01) |
| A61K 31/11 | (2006.01) |
| A61K 31/12 | (2006.01) |
| A61K 31/192 | (2006.01) |
| A61K 31/216 | (2006.01) |
| A61K 31/4525 | (2006.01) |

(52) U.S. Cl.
CPC ............ *A61K 31/137* (2013.01); *A61K 31/05* (2013.01); *A61K 31/085* (2013.01); *A61K 31/09* (2013.01); *A61K 31/11* (2013.01); *A61K 31/12* (2013.01); *A61K 31/121* (2013.01); *A61K 31/192* (2013.01); *A61K 31/216* (2013.01); *A61K 31/235* (2013.01); *A61K 31/353* (2013.01); *A61K 31/375* (2013.01); *A61K 31/4525* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,493,827 | A | 1/1985 | Valle |
| 5,827,852 | A | 10/1998 | Russell et al. |
| 6,180,666 | B1 | 1/2001 | Wacher et al. |
| 2001/0044411 | A1 | 11/2001 | Gelber et al. |
| 2003/0215462 | A1 | 11/2003 | Wacher et al. |
| 2003/0216413 | A1 | 11/2003 | Root-Bernstein et al. |
| 2007/0160688 | A1* | 7/2007 | Marchewitz ....... A61K 31/7048 424/725 |
| 2007/0160689 | A1 | 7/2007 | Giordano et al. |
| 2008/0020055 | A1* | 1/2008 | Monteith ............. A61K 9/2054 424/497 |
| 2008/0032937 | A1 | 2/2008 | Yu et al. |
| 2009/0317487 | A1 | 12/2009 | Hall et al. |
| 2011/0212927 | A1 | 9/2011 | Muhammad et al. |

OTHER PUBLICATIONS

Moon et al. Molecular Pharmaceutics 2007 (4) 865-872.*
Sudafed PE printout from Nov. 12, 2009.*
Atkinson et al. Eur. J. Clin. Pharmacol. (2015) 71:151-158.*
Kanfer et al., "Pharmacokinetics of Oral Decongestants", Pharmacotherapy: The Journal of Human Pharmacology and Drug Therapy, Jan. 1, 1993, vol. 13, No. 6, part 2, p. 116s-128s.

* cited by examiner

Primary Examiner — Jeffrey S Lundgren
Assistant Examiner — Michael Schmitt
(74) Attorney, Agent, or Firm — Whitham, Curtis & Cook, P.C.

(57) ABSTRACT

Presystemic metabolism in intestine of bioactives such as phenylephrine is avoided by administering a subject (human or animal) the bioactive (e.g., phenylephrine) in combination with one or more inhibitors of sulfation (e.g., sulfotransferase enzymes aka SULTs). This can also be enhanced be co-administering inhibitors of monoamine oxidases aka, MAOs, and uridine diphosphate glucoronysl transferases, aka UGTs. Preferably the inhibitors are GRAS compounds. The one or more inhibitor compounds inhibit the enzymes responsible for rapid presystemic metabolism, thus allowing the bioactives (e.g., phenylephrine) to be more readily absorbed intact into the circulatory system.

9 Claims, 4 Drawing Sheets

Figure 2A. Inhibition of 4-Methylumbelliferone Metabolism.
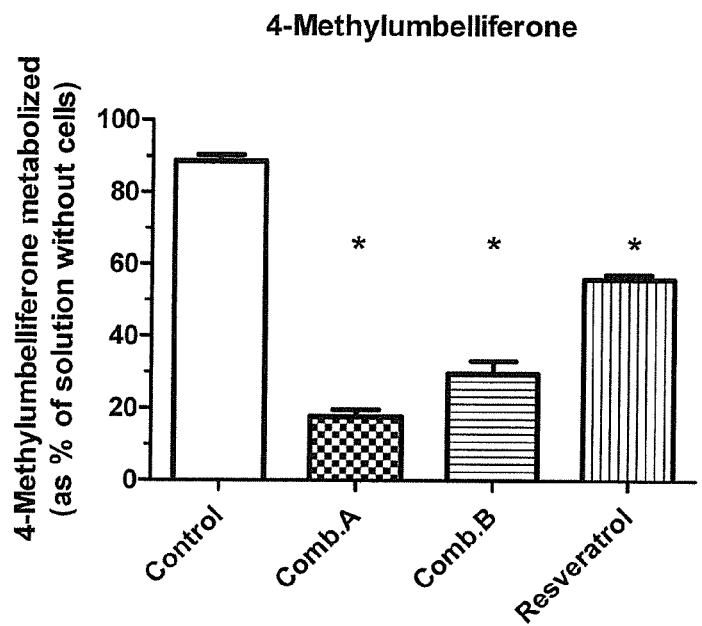
Figure 2B. Inhibition of 1-Naphthol Metabolism.
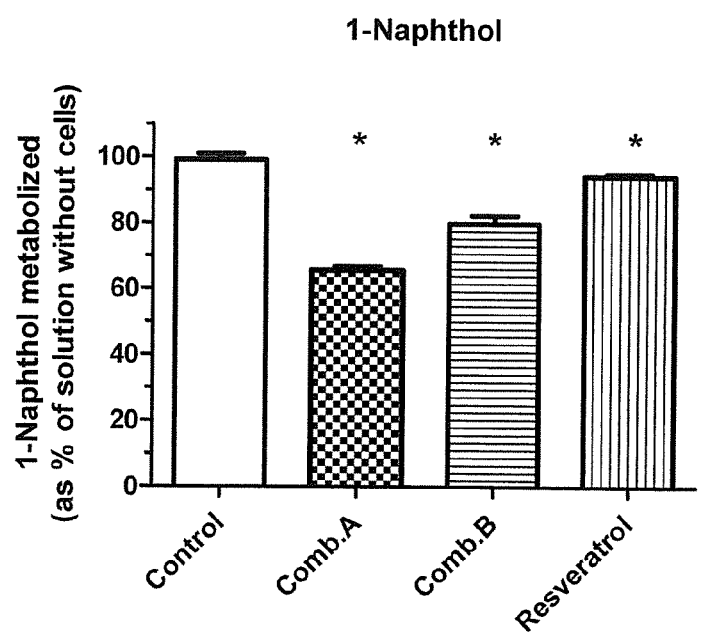

Figure 2C. Inhibition of Raspberry Ketone Metabolism.
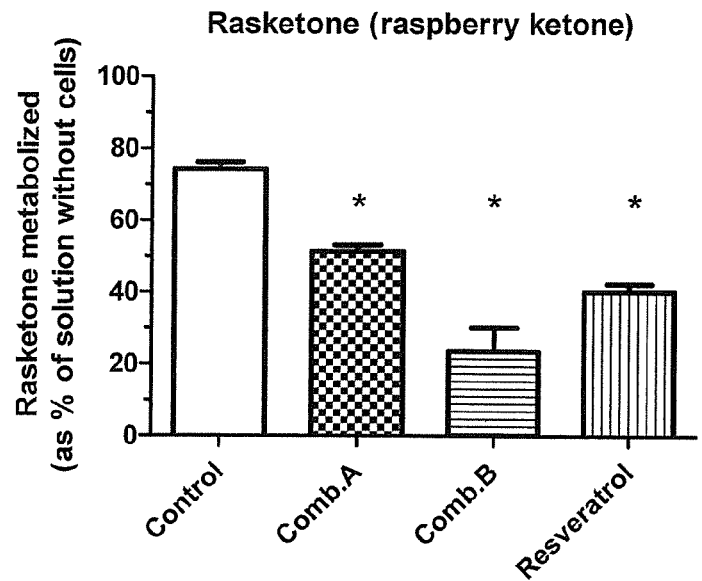
Figure 2D. Inhibition of Pinoresinol Metabolism.
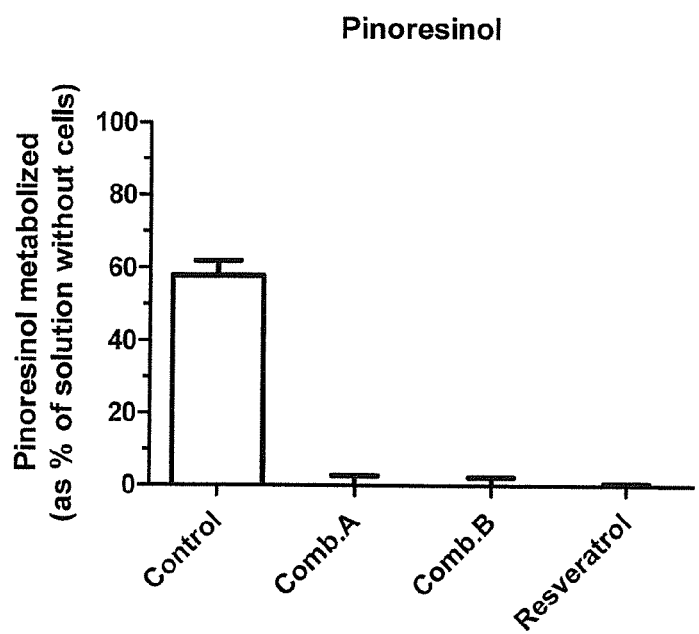

Figure 2E. Inhibition of Magnolol Metabolism.
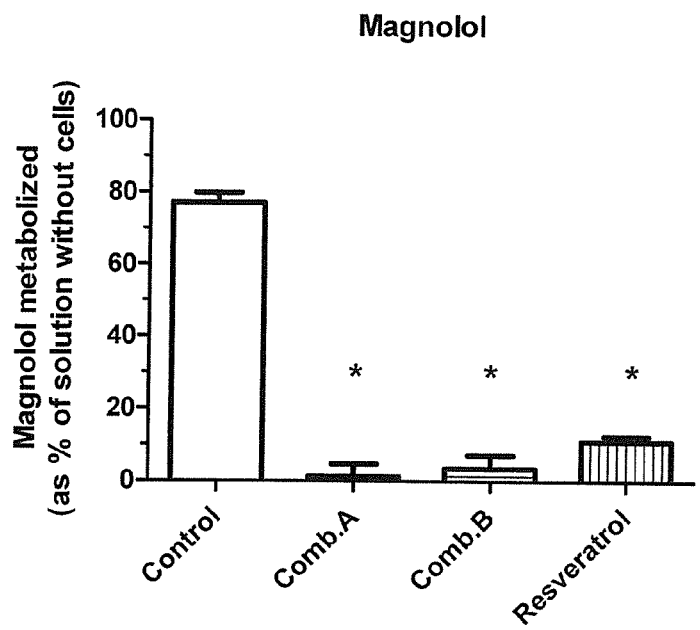
Figure 2F. Inhibition of α-Mangostin Metabolism.
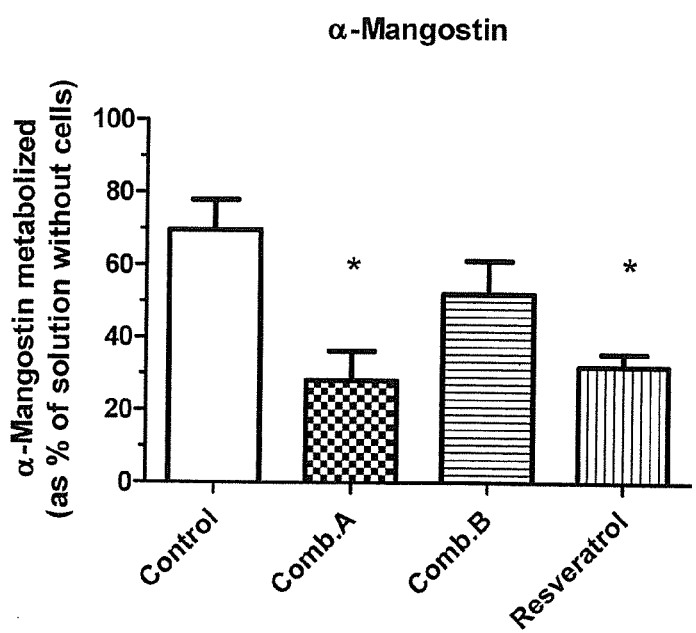

SELECTIVE METABOLIC APPROACH TO INCREASING ORAL BIOAVAILABILITY OF PHENYLEPHRINE AND OTHER PHENOLIC BIOACTIVITIES

CROSS REFERENCE TO RELATED APPLICATIONS

This application is a National Stage Application based on the International Application No. PCT/US2012/057588 filed Sep. 27, 2012 which claims priority to U.S. Provisional Application 61/539,530 filed Sep. 27, 2011 and U.S. Provisional Application 61/544,396 filed Oct. 7, 2011.

STATEMENT OF GOVERNMENT INTEREST

This invention was made with government support under contract number MD000256 awarded by the National Institutes of Health. The government has certain rights in the invention.

BACKGROUND

Field of the Invention

The invention is generally related to increasing the bioavailability of bioactive compounds which are administered or taken orally, and more particularly, to using compounds which are generally regarded as safe (GRAS), particularly certain phenolic compounds, to prevent or decrease pre-systemic or systemic metabolism or clearance of the bioactive compounds.

Description of the Prior Art

Increasing the bioavailablity of compounds provided to a subject to treat various diseases has been a subject of intense investigation for a number of years. Furthermore, there have been a number of approaches that have employed compositions that include a drug in combination with substances that are Generally Regarded As Safe (GRAS) compounds.

U.S. Pat. No. 5,972,382 to Majeed et al. teaches compositions and methods for the improvement of gastrointestinal absorption and systemic utilization of nutrients and nutritional supplements by combining them with piperine, an alkaloid derived from black pepper. Majeed does not discuss the delivery of drugs per se, and piperine is not a GRAS compound.

U.S. Pat. No. 7,576,124 to Harris describes "first-pass" inhibiting furocoumarin compounds that are purportedly safe and effective. The furocoumarins are citrus-derived substances prepared from, e.g., grapefruit. Harris does not identify which components of pre-systemic metabolism are inhibited, but the cytochrome P450 family of enzymes is referenced. The furocoumarins are not described as GRAS.

U.S. Pat. No. 7,125,564 to Chen et al. discusses problems associated with first-pass degradation of bioactive treatment compounds, and teaches the use of water-soluble complexes with glycyrrhizin, which is the main sweet-tasting compounds from licorice root. Glycyrrhizin is described as GRAS. Chen does not indicate that glycyrrhizin can inhibit first pass metabolism; rather, Chen discusses having the compositions parenterally administered to avoid the first-pass effect.

U.S. Pat. No. 7,070,814 to Qazi et al. teaches compositions which are purportedly bioenhancing/bioavailability-facilitating. These compositions include an extract and/or at least one bioactive fraction from the *Cuminum cyminum* plant (i.e., the plant from which the spice cumin is derived). This extract is combined with drugs, nutrients, vitamins, nutraceuticals, herbal drugs/products, micro nutrients, and antioxidants, along with pharmaceutically acceptable additives/excipients. Similar to the Majeed patent, Qazi discusses optionally including piperine (or extract/fraction of *piper nigrum* or *piper longum*) to purportedly increase the beneficial effect of the extract. Qazi is particularly focused on the problem of pre-systemic metabolism of drugs and suggests that the compositions described in the patent may function by inhibiting or reducing the rate of biotransformation of drugs in the liver or intestines. Qazi does not identify the extract as including GRAS compounds.

U.S. Pat. No. 6,180,666 to Wacher et al. describes orally co-administering a compound of interest with a gallic acid ester such as octyl gallate, propyl gallate, lauryl gallate, and methyl gallate. Gallic acid is a trihydroxybenzoic acid, a type of organic phenolic acid found in plants such as gallnuts, sumac, witch hazel, tea leaves, and oak bark. The gallic acid ester is purportedly present in order to inhibit biotransformations of drugs that are carried out e.g. by cytochromes P450. The esters are described as GRAS compounds.

U.S. Pat. No. 6,121,234 to Benet et al., describes a method for purportedly increasing bioavailability and reducing inter- and intra-individual variability of an orally administered hydrophobic pharmaceutical compound. In Benet, the pharmaceutical compound is orally co-administered with an essential oil or essential oil component. Benet suggests that the role of the essential oil may be to inhibit drug biotransformation in the gut. Essential oils are described as GRAS compounds.

US patent application 2003/0215462 to Wacher et al. describes using UDP-glucuronosyltrasnsferase (UGT) inhibitors to increase the bioavailability orally administered drugs. Wacher suggests the formulation may be used with 2-methoxyestradiol, raloxifene, irinotecan, SN-38, estradiol, labetalol, dilevalol, zidovidine (AZT) and morphine. The UDP-inhibitors are generally natural products and include epicatechin gallate, epigallocatechin gallate, octyl gallate, propyl gallate, quercetin, tannic acid, benzoin gum, capsaicin, dihydrocapsaicin, eugenol, gallocatechin gallate, geraniol, menthol, menthyl acetate, naringenin, allspice berry oil, N-vanillylnonanamide, clovebud oil, peppermint oil, silibinin, and silymarin. Wacher does not list resveratrol and phenylephrine as exemplary drugs, nor are the GRAS substances propyl paraben, vanillin, vitamin C and curcumin identified as being useful in Wacher. The objective of the Wacher technology appears to be the identification of specific combinations of drugs and inhibitors that work well together. Wacher notes that " . . . a compound that inhibits the glucuronidation of one substrate does not necessarily prevent the glucuronidation of all UGT substrates . . . ".

US patent applications 2006/0040875 and 2009/0093467 to Oliver et al. describe UGT2B inhibitors that can increase the bio-availability of drugs. Specifically named inhibitors are natural products such as capillarisin, isorhamnetin, β-naphthoflavone, α-naphthoflavone, hesperetin, terpineol, (+)-limonene, β-myrcene, swertiamarin, eriodictyol, cineole, apigenin, baicalin, ursolic acid, isovitexin, lauryl alcohol, puerarin, trans-cinnamaldehyde, 3-phenylpropyl acetate, isoliquritigenin, paeoniflorin, gallic acid, genistein, glycyrrhizin, protocatechuic acid, ethyl myristate, and umbelliferone. Suggested drugs for which bioavailability can be increased include morphine, naloxone, nalorphine, oxymorphone, hydromorphone, dihydromorphine, codeine, naltrexone, naltrindole, nalbuphine and buprenorphine. The focus of Oliver is on the delivery of analgesics.

US patent application 2010/0087493 to Kaivosaari et al. teaches a method for increasing bioavailability of a pharmacologically active agent that undergoes direct N-glucuronidation by UDP-glucuronosyltransferase isoenzyme UGT2B10 by administering an UGT2B10 modulator, e.g. an inhibitor of UGT2B10 (preferably selectively for UGT2B10 over UGT1A4). The drugs for which bioavailability may be increased are described as having a nucleophilic nitrogen atom, including primary, secondary and tertiary aryl- and alkylamines, sulfonamides and aromatic or aliphatic heterocyclic compounds having one or more nitrogen atoms as heteroatoms. Nicotine is identified as an example. The inhibitors are not described in detail, and only Levomedetomidine is provided as an example.

WO/2011/026112 describes methods of increase bioavailability of a pharmaceutically active agent by using specific inhibitors of a UGT that glucuronidates the pharmaceutically active agent. However, in WO/2011/026112, the inhibitors are described as comprising an N-acyl phenylaminoalcohol residue and a uridine moiety connected by a spacer. Thus, the use of GRAS compounds does not described in WO/2011/026112.

WO 2010015636 20100211 teaches beta-carbolin-derivatives to inhibit UGTs and thereby increase bioavailability of drugs such as antibiotics. However, the use of GRAS compounds for this purpose is not discussed.

Prior to the present invention, there has been little work on strategies to increase phenylephrine oral bioavailability, and no approaches which target enzymes which target phenylyephrine metabolism and which avoid enzymes which can result in toxicity and adverse effects.

SUMMARY

Phenolic compounds are commonly substrates for vigorous metabolism processes in the body of a subject, or are substrates for efflux transporters, or can function as substrates for both processes. These phenolic compounds often have rapid pre-systemic and/or systemic clearance, or insufficient tissue distribution. As a result, metabolism and transport processes often limit the medical utility of various phenolic compounds as pharmacologic agents. An embodiment of the invention uses one or more compounds to inhibit enzymes responsible for the rapid pre-systemic metabolism, and thus allows drugs to be absorbed in the body intact. Preferably, the compounds are "generally recognized as safe" ("GRAS") by the US Food and Drug Administration (FDA) or are dietary in nature. Exemplary compounds can be vitamins and nutrients such as ascorbic acid and niacin, phenolic flavoring agents such as vanillin and eugenol, antioxidants such as propylgallate and propylparaben, and dietary polyphenols such as quercetin, and combinations thereof. Compounds, and combinations of compounds, and particularly phenolic compounds useful in the practice of the invention are discussed in more detail below.

One barrier to attaining high systemic levels of a bioactive (e.g., a drug, neutraceutical, or other entity which causes and increase or decrease of an activity of interest in a cell) in a recipient is that the body (e.g. the digestive system or gut) has a number of enzymes which rapidly modify molecules prior to their entry into the circulatory system. This pre-systemic metabolism (also known as the "first-pass" effect), converts drugs to forms that are biologically less active, or even inactive, and/or which generally have low bioavailability. Examples of such enzymes include sulfotransferases (SULT's), glucuronosyltransferases (UGT's), members of the cytochrome P450 (CYP) family, catechol-O-methyltransferase (COMT), and monoamine oxidases (MAO's). By administering drugs or agents of interest together with one or more GRAS compounds or phenolic compounds or other compounds described herein which are inhibitors of these metabolic enzymes, inhibition of the enzymes can be achieved, and the drugs or other bioactive agents to be provided therewith are not modified (or are modified to a lesser extent) and retain their active form upon entering systemic circulation.

In addition, toxicity that may be associated with high doses of a bioactive compound is reduced by 1) using only GRAS compounds and 2) administering a combination of different GRAS compounds, each of which is used in lesser amounts than if administered alone. A combination may include compounds from different GRAS categories e.g. vitamins, phenolic flavoring agents, antioxidants, etc. Examples of drugs or bioactives which may be successfully administered in this manner include phenylephrine, albuterol, 2-methoxyestradiol, and (the natural products) silybin, raspberry ketone, pinoresinol, magnolol, α-mangostin, and resveratrol; however, it will be recognized by those of skill in the art that the invention can be practiced with a number of different bioactive agents.

The 2006 Stop Meth Act resulted in the substitution of phenylephrine for pseudophedrin in many high volume over the counter (OTC) products. Unfortunately, many patients have been unsatisfied with phenylephrine products, and this is likely due to low oral bioavailability. An embodiment of this invention pertains to a strategy to improve the absorption of phenylephrine using a safe and selective approach to inhibit phenylephrine metabolism. Since the availability of pseudoephedrine for non-prescription usage has been limited, many cold/flu products have been substituted with phenylephrine. However, phenylephrine has low oral bioavailability (<38%) and erratic absorption. (Hengstmann and Goronzy, 1982; Kanfer et al., 1993; Stockis et al., 1995) Phenylephrine is extensively presystemically metabolized by three major metabolic pathways: sulfation (mostly in the gut), oxidative deamination, and glucuronidation, and of these sulfation is the major route. (Hengstmann and Goronzy, 1982) Due to its low oral bioavailability, an embodiment of this invention employs a strategy that increases the bioavailability, and thus clinical efficacy, of an oral phenylephrine product.

The specific enzyme isoforms responsible for metabolizing phenylephrine in humans have not been clearly established, despite decades of clinical utility. However, one may infer its metabolic route from available data. First, the major metabolite of phenylephrine (PE) following an oral dose is phenylephrine-3-O-sulfate (PE-3S), but when the drug is given intravenously it is mainly oxidatively deaminated. (Hengstmann and Goronzy, 1982) As a result, it is inferred that the sulfotransferases (SULTs) in the intestinal wall are mainly responsible for phenylephrine sulfation. As a phenolic monoamine, PE bears structural similarities with compounds such as dopamine, serotonin, and terbutaline which are good substrates for SULT isoform 1A3 (SULT1A3). (Pacifici and Coughtrie, 2005) Furthermore, other data show that SULT1A3 protein is more highly expressed and has higher enzymatic activity in the small intestine compared to the liver, where it is very low or absent. (Pacifici and Coughtrie, 2005; Riches et al., 2009) Besides catecholamines, SULT1A3 also conjugates many monoamines including serotonin and the β-adrenergic agonists such as salbutamol (albuterol) and terbutaline. (Pacifici and Coughtrie, 2005) In fact, SULT1A3 has been proposed as the causative factor in the very low oral bioavailability (14±2%) of terbutaline. (Pearson and Wienkers, 2009)

In an embodiment of the invention, one or more inhibitor compounds (e.g. SULT, UGT, CYP, COMT and/or MAO inhibitors) are combined with a bioactive (e.g., phenylephrine). On oral administration of the combination to a subject (e.g., human or animal), the one or more inhibitor compounds inhibit the enzymes responsible for the rapid pre-systemic metabolism, thus allowing the drug to be absorbed intact. The inhibitor compounds are preferably chosen from the FDA's list of GRAS compounds, or the FDA's list of food additives (EAFUS), or other dietary compounds including dietary supplements. Combinations of inhibitor compounds can be used to synergize inhibitory effects while minimizing toxicity of each compound used. Combinations of compounds from the same or different categories (including but not limited to vitamins and nutrients such as ascorbic acid and niacin; phenolic flavoring agents such as vanillin and eugenol; antioxidants such as propylgallate and propylparaben; and dietary polyphenols such as quercetin) can be used.

In an exemplary embodiment of the invention, a subject (human or animal) is provided with an oral dose of a bioactive in combination with one or more enzymatic inhibitors (sulfotransferases (SULTs), glucouronosyltransferases (UGTs), members of the cytochrome P450 (CYP) family, catechol-o-methyltransferases (COMTs), and monoamine oxidases (MAOs)). Exemplary bioactives can include phenylephrine, albuterol, 2-methoxyestraodiol, silybin, raspberry ketone, pinoresinol, magnolol, α-mangostin, resveratrol, raloxifene, estradiol, ethinyl estradiol, terbutaline, etilephrine, synephrine, octopamine, pterostilbene, mangiferin, puerarin, salvianolic acid A, tyrosol, honokiol, marsupsin, irigenin, caffeic acid phenethyl ester (CAPE), nimbidiol, dobutamine, prenalterol, ritodrine, nadolol, labetalol, isoproterenol, L-dopa, methyldopa, salsolinol, hordenine, rosmarinic acid, ellagic acid, emodin, and amentoflavone. In some embodiments the one or more bioactives are present in a dose ranging from 0.1 mg to 200 mg, and said one or more enzymatic inhibitors are present in a dose ranging from 0.25 mg to 225 mg.

DESCRIPTION OF THE DRAWINGS

FIGS. 2A-F are graphs showing test results for various compounds incubated with LS180 cells as described above in the absence or presence of inhibitor treatment combinations A or B (see Example 4)

DETAILED DESCRIPTION

Figure 1:
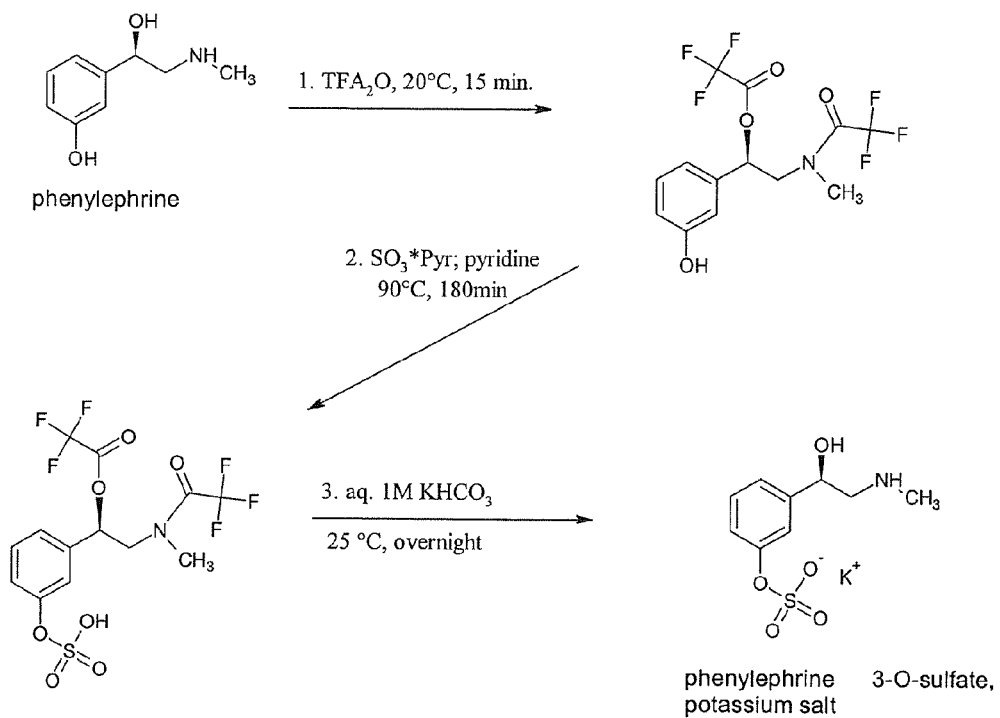
FIG. 1 is a schematic drawing of a synthesis procedure

SULT1A3 is a major isoform highly expressed in the intestine, but poorly expressed (or undetectable) in the liver. (Riches et al., 2009) Furthermore, the activity of human gastrointestinal SULTs has been characterized, and the dopamine sulfation activity (which includes SULT1A3 and 1A1) was much higher in the small intestine than the stomach or colon; it was also three-fold higher than the liver. (Chen et al., 2003) These data have been considered and integrated into pharmacokinetic models, which assert that intestinal sulfation (particularly mediated by SULT1A3) is the major determinant of pre-systemic metabolism of terbutaline and salbutamol (albuterol). (Mizuma et al., 2005; Mizuma, 2008)

Additionally, SULT1A1 is expressed in both the small intestine and the liver, although its expression and activity are higher in the liver, and it exhibits a more general substrate selectivity toward phenols. (Pacifici and Coughtrie, 2005) Furthermore, SULT1B1 is the most highly expressed isoform in the human intestine, and is capable of sulfating thyroid hormones as well as other prototypical SULT substrates including 1-naphthol and p-nitrophenol; beyond this, its substrate selectivity is poorly understood. (Riches et al., 2009) SULT2A1 is also expressed in the human intestine and sulfates phenols. (Riches et al., 2009) Other SULTs are expressed at low levels in the intestine and/or do not accept phenols/monoamines as substrates. (Pacifici and Coughtrie, 2005; Riches et al., 2009)

From the data discussed above, the inventors of the present invention infer that SULTs (including isoforms 1A1, 1B1, 2A1, and especially 1A3) play an important role in the intestinal presystemic metabolism of phenylephrine, and may play an important role in the intestinal presystemic metabolism of a number of other bioactives. The approach for increasing the bioavailability of phenylephrine (or other bioactive) described herein operates on the premise that intestinal SULT activity is the major determinant of presystemic metabolism of phenylephrine, and that inhibiting intestinal SULT results in a significant increase in oral bioavailability of phenylephrine (or other bioactives, e.g., 2-methoxyestrodiol, resveratrol, etc.). To increase bioavailability of a bioactive, a sufficient quantity of one or more SULT inhibitors should be combined with the bioactive (e.g., PE), so that the when the combination is taken orally, a greater amount of the PE remains intact for absorption into the circulatory system than if the SULT inhibitors were not included.

An oral dose of PE is substantially glucuronidated to form phenylephrine-3-O-glucuronide (PE 3G). (Hengstmann and Goronzy, 1982) As with the other metabolic pathways, it is not known which isoform of uridine diphosphate glucuronosyltransferase (UGT) is most responsible for the glucuronidation of PE in either the intestine or the liver. However, since UGT1A1, 1A6, and 1A9 glucuronidate phenols, serotonin, and propofol (respectively), (Court, 2005) their activity toward phenylephrine may be inferred. Inhibition of intestinal and/or hepatic UGTs may help to improve the oral bioavailability of phenylephrine, and this approach may also be effective with other bioactives. In some applications, combining one or more inhibitors of SULTs with one or more inhibitors of UGTs may be advantageous for increasing the bioavailability of bioactives. To increase bioavailability of a bioactive, a sufficient quantity of one or more SULT inhibitors and one or more UGT inhibitors should be combined with the bioactive (e.g., PE), so that the when the combination is taken orally, a greater amount of the PE remains intact for absorption into the circulatory system than if the SULT inhibitors and/or UGT inhibitors were not included.

In addition, monoamine oxidase isoforms A and B (MAO-A and MAO-B) are implicated in the oxidative deamination of phenylephrine. (Kanfer et al., 1993) As a result, phenylephrine is contraindicated in patients taking monoamine oxidase inhibitors, including selegiline, pargyline, and clorgyline for various psychiatric and neurological conditions. (Lexi-Comp Online) It is not known whether MAO-A or MAO-B plays a more important role in phenylephrine metabolism. However, upon intravenous PE dosing, the metabolism of PE occurs mainly through oxidative deamination to form 3-hydroxymandelic acid (3HMA), (Hengstmann and Goronzy, 1982) suggesting the liver's role in this pathway. As a result, inhibition of MAO enzymes in the intestine alone may not significantly improve the oral bioavailability of phenylephrine (or other bioactives). Furthermore, inhibition of MAO in the intestine and the liver should be avoided to minimize the possibility of adverse effects of dietary and biogenic amines on the nervous system. Therefore, in an embodiment of the inventive strategy set forth herein avoids compounds with MAO inhibition. However, in some applications, combining one or more inhibitors of SULTs with one or more inhibitors of MAOs may be advantageous for increasing the bioavailability of bioactives. To increase bioavailability of a bioactive, a sufficient quantity of one or more SULT inhibitors and one or more MAO inhibitors should be combined with the bioactive (e.g., PE), so that the when the combination is taken orally, a greater amount of the PE remains intact for absorption into the circulatory system than if the SULT inhibitors and/or MAO inhibitors were not included.

Interpreting the data published by Hengstmann, the mass balance of total radioactivity excreted into urine following an oral dose was 92% of what was recovered following an intravenous dose, so that phenylephrine would therefore be considered a "high permeability" compound. (Hengstmann and Goronzy, 1982; Amidon et al., 1995) Combining this with its high aqueous solubility, phenylephrine would be classified as a Biopharmaceutical Classification System (BCS) class 1 compound. (Amidon et al., 1995) As a BCS class 1 compound, PE disposition is expected mainly to be due to metabolism, and formulation changes which do not affect dissolution are not expected to change bioavailability. (Amidon et al., 1995; Wu and Benet, 2005) Therefore, to improve the oral bioavailability of PE, a metabolism-targeted approach would be most useful.

As a result, a premise of the inventive approach to improve PE (or other bioactive) bioavailability described herein is to escape the intestinal presystemic metabolism. An aspect of the strategy selectively inhibits the enzymes in the gut metabolizing PE, without affecting their activity in the liver. In such a way, oral bioavailability of PE would be increased, while adverse drug interactions or systemic toxicity would be avoided.

Preferred inhibitors would have similar solubility compared to PE, and would not exhibit toxicities of their own. Furthermore, they would not inhibit the systemic metabolism of neurotransmitters (dopamine, norepinephrine, serotonin) so that adverse effects on the central nervous system and the cardiovascular system could be avoided. Compounds on the FDA "generally recognized as safe" (GRAS) list, as well as certain food additives ("everything added to food in the United States," EAFUS) and dietary supplements (DS), would be likely to be safe, and facilitate regulatory approval.

The inhibitors which can be used in the practice of the invention are wide ranging. Tables 1 and 2 show results with a number of different compounds which can function as inhibitors of SULT, MAO, CYP, COMT or UGT enzymes, or which otherwise may be used to increase the bioavailability of the exemplary bioactive phenylephrine. Table 1 shows the effect of combinations of phenolic compounds for inhibiting PE metabolism as indicated by a decrease in PE disappearance, and Table 2 shows the same effect as indicated by the loss of PE sulfate formation. In Tables 1 and 2, human LS180 intestinal cells were used for screening the inhibition of PE metabolism. For the experiment which produced the results in Table 1, the concentration of PE was 50M; the concentration of vitamin C (where present) was 1 mM; the total concentration of other inhibitors was 100 µM. Cells were incubated at 37° C. for 14 to 17.5 hours, as indicated. The LS180 model provides an inexpensive method to imitate the human intestine, with regards to PE metabolism. Unlike animal models or recombinant enzymes, this system has the advantages of being of human origin (thus avoiding species differences) and including some consideration of the ability of the inhibitors to cross the cell membranes and reach the enzymes. For the LS180 experiments, LS180 cells are seeded at the concentration of $1.9 \times 10^5$ cells/ml in 12-well plate. Cells are incubated with 0.5 ml DMEM containing 1% non-essential amino acid (pH 7.4) with phenylephrine (50 µM)/inhibitor (100 µM) (except ascorbic acid: 1000 µM) for 14 hr to 17.5 hr at 37° C. with 5% $CO_2$. After incubation, medium is removed and stored at −80° C. until analysis. The metabolic reactions are quenched by placing 12-well plate on ice and quickly rinsing each well. The cell extraction of metabolites is carried out with 1 ml 2% acetic acid solution in methanol. Cells are scraped and collected in centrifuge tubes. The suspension is mixed for 2-3 min and centrifuged at 18,000 rcf for 5 min. Supernatants (800 µl) are collected. After scraping, each well is washed twice as above. The washing solution is collected with the supernatant and dried under reduced pressure. The residue is re-suspended in 35 µl water and analyzed by HPLC. All the samples are analyzed for PE by HPLC with a phenyl column (150×3.2 mm, 5 µm, 55° C.) at the flow rate of 0.75 ml (20% methanol and 80% (aqueous 1% acetic acid)) and detected by fluorescence (excitation 270 nm, emission 305 nm). The data are processed with one-way ANOVA followed by Dunnett's post test; * indicates $p<0.05$.

TABLE 1

Table 1: Extent of PE (50 µM) Disappearance with Phenolic Dietary Compounds

| Compound | Extent of PE Disappearance (as % of control) | SD | Incubation Time (hr) |
|---|---|---|---|
| propylparaben | 53.80% | 75.30% | 14 |
| propylparaben + ascorbic acid | 56.40% | 77.90% | 14 |
| vanillin | 90.20% | 42.30% | 14 |
| propyl gallate | 114.30% | 48.50% | 14 |
| *curcumin | 24.50% | 24.20% | 17 |
| *eugenol + propylparaben + vanillin + ascorbic acid | 31.10% | 18.80% | 17 |
| *propylparaben + vanillin | 37.00% | 19.40% | 17 |
| *eugenol + propylparaben | 42.60% | 14.50% | 17 |
| *zingerone | 52.40% | 25.20% | 17 |
| methylparaben | 75.90% | 24.30% | 17 |
| ethylvanillin | 76.50% | 19.10% | 17 |
| *resveratrol | 14.20% | 48.50% | 17.5 |
| quercetin | 48.70% | 16.00% | 17.5 |
| *eugenol + vanillin | 57.50% | 35.70% | 17.5 |
| naringin | 75.70% | 14.40% | 17.5 |
| eugenol | 133.00% | 52.70% | 17.5 |
| *curcumin + resveratrol | 0.00% | — | 18.5 |
| *curcumin + pterostilbene + resveratrol + zingerone | 0.00% | — | 18.5 |
| *pterostilbene + zingerone | 36.50% | 12.20% | 18.5 |
| *guaiacol | 51.30% | 13.90% | 18.5 |
| *pterostilbene + zingerone | 41.80% | 7.40% | 19 |
| *pterostilbene | 70.60% | 7.20% | 19 |
| *isoeugenol | 73.90% | 7.50% | 19 |

TABLE 2

Inhibition of PE Sulfate Formation with Phenolic Dietary Compounds

| Compound | PE Sulfate Formation (as % of control) | SD | Incubation Time (hr) |
|---|---|---|---|
| *guaiacol | 33.00% | 7.34% | 18.5 |
| *curcumin + resveratrol | 0.10% | — | 18.5 |
| *pterostilbene + zingerone | 28.30% | 4.49% | 18.5 |
| *curcumin + pterostilbene + resveratrol + zingerone | 0.70% | — | 18.5 |

These results in Tables 1 and 2 demonstrate the extent to which exemplary combinations of inhibitors inhibit the metabolism of phenylephrine (PE) in the LS180 intestinal cell culture model. Note that some combination treatments were more effective than single agent treatments. While vanillin and eugenol failed to inhibit PE metabolism alone, in combination together or with other agents they significantly and synergistically inhibited it. Curcumin and resveratrol were more effective in combination(s).

In connection with the data above, FIG. 1 illustrates an exemplary synthesis route for phenylephrine 3-O-Sulfate. Phenylephrine 3-O-sulfate was dissolved in 2 molar equivalents of trifluoroacetic anhydride and incubated at room temperature for 15 minutes to protect the alkyl hydroxyl and the secondary amine. The product was purified by silica gel chromatography. It was then dissolved in pyridine with 3-4 molar equivalents of pyridine-sulfur trioxide complex with heat and stirring. Pyridine was evaporated, followed by hydrolysis in aqueous potassium bicarbonate at room temperature overnight, and purified by HILIC-amide chromatography. LC-MS/MS (ESI−) reveals a 246>166 mass transition indicating the loss of SO3 from the phenol. This synthesis enables the detection of the main metabolic product of the SULT enzyme activity on phenylephrine, as shown in Table 2.

In addition to the compounds and combinations of compounds indicated to have inhibitory capacity, and thus, the capacity to increase the bioavailability of PE (as well as other bioactives), other compounds which may be employed to increase the bioavailability of orally provided bioactives may be selected from methyl paraben, ethyl paraben, propyl paraben, butyl paraben, (−)-Homoeriodictyol; 2,6-dimethoxyphenol; 2-isopropylphenol; 2-methoxy-4-methylphenol; 2-methoxy-4-propylphenol; 4-(1,1-dimethylethyl)phenol; 4-allylphenol; 4-ethylguaiacol; 4-ethylphenol; anisyl alcohol; butylated hydroxyanisole; butylated hydroxytoluene; carvacrol; carveol; dimethoxybenzene; divanillin; essential oils+extracts (e.g., clove, cinnamon, nutmeg, rosemary, citrus, vanilla, ginger, guaiac, turmeric, grape seed, black pepper, etc.); ethyl p-anisate; eugenyl acetate; eugenyl formate; isoeugenol (acetate, formate, or benzoate); L-tyrosine; methyl anisate; methylphenyl ether; methylphenyl sulfide; O-(ethoxymethyl)phenol; O-cresol; O-propylphenol; resorcinol; salicylates (amyl, benzyl, butyl, ethyl, methyl, etc.); thymol; trans-anethole; vanillin propylene glycol acetal; vanillyl acetate; vanillyl alcohol; vanillyl ethyl ether; vanillylidene acetone; veratraldehyde; and xylenols (2,6-; 2,5-; 3,4-). Other herbal/natural compounds not on GRAS/EAFUS list which may be used to increase the bioavailability of orally provided bioactives include hesperetin; eriodictyonone; 5,3'-Dihydroxy-7,4'-dimethoxyflavanone; isorhamnetol; tamarixetin; syringetin; 3',7-Dimethylquercetin; and methylated and/or dehydroxylated analogs of quercetin.

Other flavonoids which may be used include but are not limited to flavanols (such as catechin, gallocatechin, epicatechin, catechin gallate, gallocatechin gallate, epigallocatechin, epicatechin gallate, epigallocatechin gallate, leucoanthocyanidin, and proanthocyanidins), flavones (such as luteolin, apigenin, tangeretin), flavonols (such as quercetin, kaempferol, myricetin, fisetin, isorhamnetin, pachypodol, rhamnazin), flavanones (such as hesperetin, hesperidin, eriodictyol, homoeriodictyol), flavanonols (such as taxifolin, dihydroquercetin, dihydrokaempferol), anthocyanidins (such as anthocyanidin, cyanidin, delphidin, malvidin, pelargonidin, peonidin, petunidin), isoflavones (such as genistein, daidzein, glycitein), isoflavanes (such as equol, lonchocarpane, laxiflorane), and neoflavonoids (such as dalbergin, nivetin, coutareagenin, dalbergichromene). Glycosides of the flavanols, flavonol, flavones, flavanones, flavanonols, anthocyanidins, isoflavones, isoflavanes, and neoflavonoids may also be used.

Flavonolignans (such as silybin, silybinin A, silybin B, silydianin, silychristin, isosilychristin, isosilybin A, isosilybin B, silibinin, silychristin, silydianin, dehydrosilybin, deoxysilycistin, deoxysilydianin, silandrin, silybinome, silyhermin and neosilyhermin, silyamandin, hydnocarpin, scutellaprostin A, B, C, D, E and F; hydnowightin, palstatin, salcolin A and salcolin B, rhodiolin) and their glycosides may also be used in the practice of the invention. Lignans (pinoresinol, steganacin, enterodiol, enterolactone, lariciresinol, secoisolariciresinol, matairesinol, hydroxymatairesinol, syringaresinol and sesamin) and their glycosides would be included. Xanthones (alpha-mangostin, beta-mangostin, gamma-mangostin, garcinone, garcinone A, garcinone C, garcinone D, mangostanol, gartanin) and their glycosides may be used in the practice of the invention. Miscellaneous natural phenolic compounds may also be included such as hydroxy-methoxy-coumarins, hydroxychalcones, biochanin A, prunetin, kavalactones (11-hydroxyyangonin; 11-methoxy-12-hydroxydehydrokavain; 5-hydroxykavain), ellagic acid, rosmarinic acid, emodin, and amentoflavone.

Furthermore, suitable inhibitory compounds for use in the practice of the invention can be readily identified using enzymatic activity assays. Exemplary assays are set forth below:

SULTs:

Selected recombinant SULT isoforms (including 1A1, 1A3, 1B1, 2A1) are available commercially from a variety of sources including Xenotech. Appropriate control substrates should be used; for example, 4-methylumbelliferone for SULT1A1 and 1B1; 1-naphthol for SULT1A3; estradiol for SULT2A1. (Pacifici and Coughtrie, 2005) Assays should be performed according to the manufacturer's instructions (Cypex/Xenotech LLC). Briefly, substrates should be incubated at 37° C. in the presence or absence of 3'-phosphoadenosine 5'-phosphosulfate (PAPS; 20 μM) in 50 mM potassium phosphate buffer (pH 7.4) containing 5 mM magnesium chloride and 10 mM dithiothreitol. Initial substrate concentration should be 2 μM, with a protein concentration of 2.5 μg/ml, incubating for 5-60 minutes. Reactions should be stopped with acetonitrile, and analyzed by reversed-phase HPLC to determine disappearance of the control substrate (and/or formation of the metabolites), and PE (or other bioactive) and/or their metabolites should be analyzed.

UGTs:

Selected recombinant UGT isoforms (including 1A1, 1A6, 1A9) are commercially available from a variety of sources including BD Biosciences. Appropriate control substrates should be used; for example, estradiol, 1-naphthol, and propofol should be used as control substrates for UGT1A1, 1A6, and 1A9, respectively. (Court, 2005) Determinations should be performed in Tris-HCl buffer (50 mM; pH 7.5) containing magnesium chloride 8 mM, alamethicin 25 µg/ml, incubated at 37° C. in the presence or absence of 2 mM uridine 5'-diphospho-glucuronic acid (UDPGA). Initial substrate concentration should be 1 µM, with a protein concentration of 200 µg/ml, incubating for 5-60 minutes.

MAOs:

Recombinant MAO isoforms (A and B) are commercially available from a variety of sources including BD Biosciences. Appropriate control substrates should be used; for example, kynuramine is a substrate of both isoforms forming a fluorescent product by oxidative deamination. (Herraiz and Chaparro, 2006) Determinations should be performed in 100 mM potassium phosphate buffer (pH 7.4), incubated at 37° C. The initial substrate concentrations should be 1 µM, with a protein concentration of 50 µg/ml, incubating for 5-60 minutes.

While the data are particularly compelling in terms of showing that certain inhibitory compounds or combinations of compounds can prevent the metabolism of phenylephrine, the invention may be practiced with a variety of other bioactives including the following: albuterol, raloxifene, estradiol, ethinyl estradiol, terbutaline, etilephrine, synephrine, octopamine, resveratrol, pterostilbene, magnolol, mangiferin, puerarin, resveratrol, salvianolic acid A, rasketone (a.k.a. "raspberry ketone"), tyrosol, honokiol, marsupsin, irigenin, caffeic acid phenethyl ester (phenylethyl caffeate; "CAPE"), and nimbidiol.

Clinically, the inhibitors utilized in the practice of the invention are preferably acceptable to regulatory bodies (such as the FDA) and without adverse effects. For example, the acceptable daily intake of eugenol, ethyl vanillin, and vanillin are 2.5, 3.0, and 10 mg/kg/day, respectively (Fenaroli, 2010). As another example, pterostilbene is FDA approved as a GRAS compound in dosages of 30 mg/kg/day. Quercetin is a GRAS substance which is also marketed as a dietary supplement in dosages reaching 500 mg/day, while resveratrol and curcumin as dietary supplements are used in doses of 250 mg or 500 mg/day, respectively. Propylparaben is FDA-approved as an antioxidant/preservative food additive amounting to 0.1% w/w food fat content, thus individual dosages in excess of 10 mg are expected to be permissible. Doses of each inhibitor is expected to be such that when dissolved in GI fluid (250 ml) concentration will be between 10-3000 µM: minimum dose=2.5 µmol (0.25-0.75 mg); maximum dose=750 µmol (75-225 mg), assuming approximate molecular weights of inhibitors in the range of 100-300 Daltons. Bioactive ingredients would be dosed ranging from 0.5 to 200 mg, depending upon the compound and the therapeutic application.

Many natural phenolic compounds have very low oral bioavailability, thus they often fail to result in clinical benefits. This technology would enable the biological activities of many natural phenolic compounds to be realized by inhibiting their presystemic metabolism thereby improving their oral bioavailability. Examples of clinical utilities would include diabetes (especially pre-diabetes and type 2 diabetes), heart disease (including hyperlipidemia), liver disease (including cholestasis and hepatoprotection), obesity, metabolic syndrome, various cancers, inflammatory diseases (including arthritis), and anti-aging (antioxidant) activities.

EXAMPLES

Example 1

In Vitro Inhibition of Phenylephrine (PE) Sulfation by Phenolic Dietary Compounds Background.

This in vitro study aimed to investigate the feasibility of inhibiting the pre-systemic sulfation of PE.

Methods.

Phenolic compounds were selected from FDA's "GRAS" list, approved food additives, or dietary supplements. LS180 cells were used as a model to test the effect of these phenolic compounds on the pre-systemic sulfation of PE. The cells were incubated in 0.5 ml medium with PE (50 µM)±inhibitor (100 µM) overnight. Extracellular buffer was collected and cells were extracted with methanol. PE was determined by reversed-phase HPLC with fluorescence detection. The formation of PE-sulfate was analyzed by LC-MS/MS. Results (n=3 per group) were analyzed by one-way ANOVA with Dunnett's post-test (p<0.05; Prism 5).

Results.

The extent of disappearance of PE (control=503±127 pmol/hr) was significantly (p<0.05) decreased to the following (mean±SD, as % of control): curcumin 24±24%, guaiacol 51±14%, isoeugenol 74±8%, pterostilbene 71±7%, resveratrol 14±48%, zingerone 52±25%, and the combinations eugenol+propylparaben 43±15%, vanillin+propylparaben 37±19%, eugenol+propylparaben+vanillin+ascorbic acid 31±19%, eugenol+vanillin 58±36%, and pterostilbene+zingerone 37±12%. The combinations of curcumin+resveratrol and curcumin+pterostilbene+resveratrol+zingerone almost completely inhibited PE disappearance. Correspondingly, PE-sulfate formation was inhibited by guaiacol to 33±7% (control=100%; 6650±260 µV*s) and by pterostilbene+zingerone to 28±4%. The combinations of curcumin+resveratrol and curcumin+pterostilbene+resveratrol+zingerone inhibited ≥99% of PE-sulfate formation. However, when propyl gallate, vanillin, or eugenol was used alone, they had no significant effect on PE disappearance, suggesting synergy when vanillin or eugenol was used with other compounds.

Conclusion.

Several compounds and combinations including resveratrol inhibit the pre-systemic sulfation of PE and can improve its oral bioavailability.

Example 2

Resveratrol (RES; 25 µM) was incubated with LS180 cells for 4 hours (as described in Example 1) in the absence or presence of the inhibitors (100 µM) listed below. The compounds marked with asterisks indicate a significant inhibition of resveratrol metabolism (disappearance) compared to controls in the absence of the inhibitors. Methylparaben and ethyl vanillin showed the greatest extent of inhibition of resveratrol metabolism, while cinnamic acid, piperine, eugenol, vanillin, propylgallate, and propylparaben also showed significant inhibition.

TABLE 3

Extent of Resveratrol Disappearance with Phenolic Dietary Compounds.

| Compound | Extent of RES Disappearance (as % of control) | SD | Incubation Time (hr) |
|---|---|---|---|
| *methylparaben | 0.4% | n/a | 4 |
| *ethylvanillin | 8.1% | 377.0% | 4 |
| *cinnamic acid | 16.3% | 63.8% | 4 |
| *piperine | 26.4% | 67.6% | 4 |
| *eugenol | 38.3% | 25.8% | 4 |
| *vanillin | 44.8% | 16.6% | 4 |
| *propyl gallate | 51.2% | 14.5% | 4 |
| *propylparaben | 57.8% | 20.1% | 4 |
| *sinapic acid | 86.1% | 11.7% | 4 |
| zingerone | 83.7% | 40.9% | 4 |
| caffeic acid | 91.1% | 9.3% | 4 |
| ferulic acid | 100.2% | 37.9% | 4 |
| vanillic acid | 102.9% | 37.4% | 4 |

Example 3

2-Methoxyestradiol (2-ME; 10 µM) was incubated with LS180 cells for 4 hours (as described above) in the absence or presence of the inhibitors (100 µM) listed below. The compounds marked with asterisks indicate a significant inhibition of 2-methoxyestradiol metabolism (disappearance) compared to controls in the absence of the inhibitors. Significant inhibition of 2ME metabolism was observed with eugenol, vanillin, propyl gallate, and propylparaben.

TABLE 4

Extent of 2-Methoxyestradiol Disappearance with Phenolic Dietary Compounds

| Compound | Extent of 2-ME Disappearance (as % of control) | SD | Incubation Time (hr) |
|---|---|---|---|
| *eugenol | 21.2% | 54.8% | 1 |
| *eugenol | 33.9% | 26.9% | 1 |
| *vanillin | 39.4% | 21.4% | 1 |
| *propyl gallate | 42.8% | 24.7% | 1 |
| *propyl gallate | 50.4% | 14.1% | 1 |
| *vanillin | 51.2% | 14.5% | 1 |
| *propylparaben | 51.7% | 20.6% | 1 |
| *propylparaben | 57.7% | 13.7% | 1 |
| cinnamaldehyde | 87.6% | 13.1% | 1 |
| cinnamaldehyde | 93.9% | 9.0% | 1 |
| *sinapic acid | 88.1% | 10.4% | 1 |
| caffeic acid | 93.3% | 10.0% | 1 |
| vanillic acid | 99.1% | 7.9% | 1 |
| gallic acid | 101.5% | 10.8% | 1 |
| ferulic acid | 101.7% | 10.2% | 1 |

Example 4

Compounds were incubated with LS180 cells as described above in the absence or presence of inhibitor treatment combinations A or B or resveratrol. Combination A comprises quercetin 50 µM, ethyl vanillin 25 µM, isoeugenol 25 µM, and propylparaben 25 µM; Combination B comprises 25 µM each of resveratrol, curcumin, zingerone, and pterostilbene; the 3rd treatment is resveratrol 100 µM. The compounds, their concentrations, and incubation times were 4-methylumbelliferone (1 µM; 1.5 hrs.; FIG. 2A), 1-naphthol (1 µM, 0.5 hrs; FIG. 2B), raspberry ketone (2.5 µM, 15 hrs.; FIG. 2C), pinoresinol (1 µM, 1.5 hrs.; FIG. 2D), magnolol (1 µM, 1.5 hrs.; FIG. 2E), and α-mangostin (1 µM, 1.5 hrs.; FIG. 2F). To control for any effects of the inhibitors on the stability of the compounds, solutions lacking LS180 cells were incubated under the same conditions and used to correct for the expected concentrations of the compounds in the absence of metabolism. Samples were analyzed by reversed phase HPLC with ultraviolet and/or fluorescence detection, results were compared by one-way ANOVA with Dunnett's post test. FIGS. 2A-2F show that LS180 cells were able to metabolize >50% of the compounds in the absence of any inhibitor treatment (controls). The data show that Combination A was the most effective treatment for inhibiting metabolism of 4-methylumbelliferone, 1-naphthol, pinoresinol, magnolol, and α-mangostin, while Combination B was the most effective for inhibiting metabolism of raspberry ketone.

Compounds such as raspberry ketone, pinoresinol, magnolol, and α-mangostin have preclinical biological activities which would be useful in the treatment or prevention of diseases such as hyperlipidemia, diabetes, obesity, cancer, and inflammation. However, these compounds also have very low oral bioavailability due to presystemic metabolism, which masks their clinical utility. Our data show that the inhibitor combinations described herein can decrease the intestinal metabolism of selected phenolic compounds. These phenolic natural compounds, when utilized with our inhibitor combinations to improve their oral bioavailability, can be used more effectively to achieve a clinical benefit.

Example 5

Silybin (20 µM) and albuterol hemisulfate salt (20 µM) were incubated for 15 hours with LS180 cells as described in Example 4, in the presence or absence of Combination A. Albuterol metabolism was significantly inhibited by Combination A ($p<0.05$). The appearance of an unknown metabolite of silybin was significantly inhibited by Combination A ($p<0.05$).

REFERENCES

Amidon G L, Lennernas H, Shah V P and Crison J R (1995) A theoretical basis for a biopharmaceutic drug classification: the correlation of in vitro drug product dissolution and in vivo bioavailability. *Pharm Res* 12:413-420.

Burdock G A (2005) Fenaroli's Handbook of Flavor Ingredients. 6th Edition, CRC Press, New York.

Chen G, Zhang D, Jing N, Yin S, Falany C N and Radominska-Pandya A (2003) Human gastrointestinal sulfotransferases: identification and distribution. *Toxicol Appl Pharmacol* 187:186-197.

Court M H (2005) Isoform-selective probe substrates for in vitro studies of human UDP-glucuronosyltransferases. *Methods Enzymol* 400:104-116.

Hengstmann J H and Goronzy J (1982) Pharmacokinetics of 3H-phenylephrine in man. *Eur J Clin Pharmacol* 21:335-341.

Herraiz T and Chaparro C (2006) Human monoamine oxidase enzyme inhibition by coffee and beta-carbolines norharman and harman isolated from coffee. *Life Sci* 78:795-802.

Kanfer I. Dowse R and Vuma V (1993) Pharmacokinetics of oral decongestants. *Pharmacotherapy* 13:116 S-128S; discussion 143S-146S.

Mizuma T (2008) Assessment of presystemic and systemic intestinal availability of orally administered drugs using in vitro and in vivo data in humans: intestinal sulfation metabolism impacts presystemic availability much more than systemic availability of salbutamol, SULT1A3 substrate. *J Pharm Sci* 97:5471-5476.

Mizuma T, Kawashima K, Sakai S, Sakaguchi S and Hayashi M (2005) Differentiation of organ availability by sequential and simultaneous analyses: intestinal conjugative metabolism impacts on intestinal availability in humans. *J Pharm Sci* 94:571-575.

Pacifici G M and Coughtrie M W (2005) *Human Cytosolic Sulfotransferases*. CRC Press: Taylor & Francis Group, Boca Raton, Fla.

Pearson P G and Wienkers L C (2009) *Handbook of Drug Metabolism*. Informa Healthcare, New York.

Riches Z, Stanley E L, Bloomer J C and Coughtrie M W H (2009) Quantitative Evaluation of the Expression and Activity of Five Major Sulfotransferases (SULTs) in Human Tissues: The SULT "Pie". *Drug Metab Dispos* 37:2255-2261.

Stockis A, Deroubaix X, Jeanbaptiste B, Lins R, Allemon A M and Laufen H (1995) Relative bioavailability of carbinoxamine and phenylephrine from a retard capsule after single and repeated dose administration in healthy subjects. *Arzneimittelforschung* 45:1009-1012.

Wu C Y and Benet L Z (2005) Predicting drug disposition via application of BCS: transport/absorption/elimination interplay and development of a biopharmaceutics drug disposition classification system. *Pharm Res* 22:11-23.

The invention claimed is:

1. A method of orally administering phenylephrine to a subject in need thereof so as to enhance bioavailability of phenylephrine, comprising the step of orally administering to said subject phenylephrine in combination with one or more inhibitors of one or more sulfotransferase (SULTs) in an amount effective to enhance the bioavailability of phenylephrine, wherein said one or more inhibitors of SULTs comprises resveratrol, quercetin, vanillin, and propylparaben.

2. The method of claim 1 further comprising administering to said subject one or more inhibitors of monoamine oxidases (MAOs).

3. The method of claim 1 further comprising administering to said subject one or more inhibitors of uridine diphosphate glucoronysl transferases (UGTs), wherein said one or more inhibitors of UGTs are phenols or alkylated catechols.

4. The method of claim 1 wherein said one or more inhibitors of SULTs directly inhibits SULT 1A3.

5. A method of orally administering phenylephrine to a subject in need thereof which enhances bioavailability of phenylephrine, comprising the step of administering, for oral administration, phenylephrine to said subject in combination with one or more phenols or alkylated catechols in an amount effective to enhance the bioavailability of phenylephrine, wherein said one or more phenols or alkylated catechols are selected from the group consisting of guaiacol, isoeugenol, eugenol, zingerone, vanillin, ethyl vanillin, curcumin, trans-resveratrol, trans-pterostilbene, propyl paraben, methyl paraben, and combinations thereof.

6. The method of claim 5 wherein said step of administering includes oral administration of one or more phenolic compounds which are not alkylated catechols.

7. A method of orally administering a bioactive to a subject in need thereof so as to enhance bioavailability of said bioactive, wherein said bioactive is selected from the group consisting of phenylephrine, albuterol, 2-methoxyestraodiol, silybin, raspberry ketone, pinoresinol, magnolol, α-mangostin, resveratrol, raloxifene, estradiol, ethinyl estradiol, terbutaline, etilephrine, synephrine, octopamine, pterostilbene, mangiferin, puerarin, salvianolic acid A, tyrosol, honokiol, marsupsin, irigenin, caffeic acid phenethyl ester (CAPE), nimbidiol, curcumin, zingerone, and combinations thereof, comprising the step of orally administering to said subject said bioactive in combination with one or more inhibitors which are different from said bioactive in an amount effective to enhance the bioavailability of said bioactive, wherein said one or more inhibitors are selected from the group consisting of sulfotransferases (SULTs), members of the cytochrome P450 (CYP) family, and catechol-o-methyltransferases (COMTs), wherein said one or more inhibitors of SULTs comprises resveratrol, quercetin, vanillin, and propylparaben.

8. The method of claim 3, wherein said phenols or alkylated catechols are selected from the group consisting of guaiacol, isoeugenol, eugenol, zingerone, vanillin, ethyl vanillin, curcumin, trans-resveratrol, trans-pterostilbene, propyl paraben, methyl paraben, and combinations thereof.

9. The method of claim 5, wherein two or more of inhibitors of UGTs are administered.

* * * * *